United States Patent
Price et al.

(10) Patent No.: US 6,933,312 B2
(45) Date of Patent: Aug. 23, 2005

(54) PYRAZOLE DERIVATIVES

(75) Inventors: David A. Price, Deal (GB); Matthew D. Selby, Sandwich (GB); Paul A. Stupple, Canterbury (GB)

(73) Assignee: Agouron Pharmaceuticals, Inc., La Jolla, CA (US)

( * ) Notice: Subject to any disclaimer, the term of this patent is extended or adjusted under 35 U.S.C. 154(b) by 0 days.

(21) Appl. No.: 10/669,819

(22) Filed: Sep. 23, 2003

(65) Prior Publication Data

US 2004/0133002 A1 Jul. 8, 2004

Related U.S. Application Data

(60) Provisional application No. 60/432,859, filed on Dec. 11, 2002.

(30) Foreign Application Priority Data

Oct. 7, 2002 (GB) .............................................. 0223232

(51) Int. Cl.[7] ................ A61K 31/4152; A61K 31/4155; C07D 401/06
(52) U.S. Cl. .................................... 514/406; 548/364.7
(58) Field of Search ........................ 514/406; 548/364.7

(56) References Cited

FOREIGN PATENT DOCUMENTS

| GB | 0223232.0 | 10/2002 |
|---|---|---|
| WO | WO91/11172 | 8/1991 |
| WO | WO94/02518 | 2/1994 |
| WO | WO98/55148 | 12/1998 |
| WO | WO02/04424 | 1/2002 |
| WO | WO 02/30907 | 4/2002 |
| WO | WO02/34745 | 5/2002 |
| WO | WO 02/085860 | 10/2002 |

OTHER PUBLICATIONS

U.S. Appl. No. 60/432,859, filed Dec. 11, 2002, Pfizer Inc.
Berge, et. al., "Pharmaceutical Salts," *Journal of Pharmaceutical Sciences*, 1977, 1–19, vol. 66, No. 1.
Bighley, et. al., "Salt Forms of Drugs and Absorption," *Encyclopedia of Pharmaceutical Technology*, Marcel Dekker Inc., 1996, 453–497, vol. 13, New York.
Bundgaard, et. al., *Design of Prodrugs*, 1985, Chapter 1, Elsevier Science Publishers, Amsterdam, New York, Oxford.
Ferres, et. al., "Pro–Drugs of β–Lactam Antibiotics," *Drugs of Today*, 1983, 499–538, vol. 19, No. 9.
Genin, et. al., "Novel 1,5–Diphenylpyrazole Nonnucleoside HIV–1 Reverse Transcriptase Inhibitors with Enhanced Activity Versus the Delavirdine–Resistant P236L Mutant: Lead Indentification and SAR of 3– and 4–Substituted Derivatives," *Journal of Medicinal Chemistry*, 2000, 1034–1040, vol. 43, No. 5.
Greene, et. al., *Protecting Groups in Organic Synthesis*, 1991, Second Edition, John Wiley & Sons, New York, Chichester, Brisbane, Toronto, Singapore.
Katritzky, et. al., "The Structure, Reactions, Synthesis and Uses of Heterocyclic Compounds," *Comprehensive Heterocyclic Chemistry*, 1984, vol. 1–11, Pergamon Press, Oxford, New York, Toronto, Sydney, Paris, Frankfurt.

*Primary Examiner*—Taofiq Solola
(74) *Attorney, Agent, or Firm*—Keith D. Hutchinson; Bryan C. Zielinski; Peter C. Richardson

(57) ABSTRACT

This invention relates to pyrazole derivatives of formula (I)

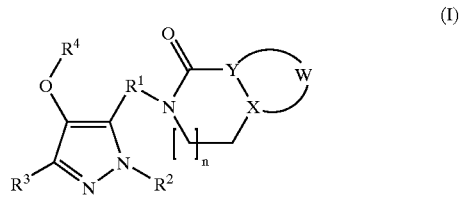

(I)

or pharmaceutically acceptable salts, solvates or derivative thereof, wherein $R^1$ to $R^4$, n W, X and Y are defined in the description, and to processes for the preparation thereof, intermediates used in their preparation of, compositions containing them and the uses of such derivatives.

The compounds of the present invention bind to the enzyme reverse transcriptase and are modulators, especially inhibitors thereof. As such the compounds of the present invention are useful in the treatment of a variety of disorders including those in which the inhibition of reverse transcriptase is implicated. Disorders of interest include those caused by Human Immunodificiency Virus (HIV) and genetically related retroviruses, such as Acquired Immune Deficiency Syndrome (AIDS).

7 Claims, No Drawings

PYRAZOLE DERIVATIVES

This application claims the benefit of U.S. Provisional Application No. 60/432,859, filed Dec. 11, 2002, and incorporates each application by reference in its entirety.

BACKGROUND OF THE INVENTION

This invention relates to pyrazole derivatives, to their use in medicine, to compositions containing them, to processes for their preparation and to intermediates used in such processes.

Reverse transcriptase is implicated in the infectious life-cycle of Human Immunodeficiency Virus (HIV). Compounds which interfere with the function of this enzyme have shown utility in the treatment of conditions caused by HIV and genetically related retroviruses, such as Acquired Immune Deficiency Syndrome (AIDS). There is a constant need to provide new and better modulators, especially inhibitors, of HIV reverse transcriptase, since the virus is able to mutate, becoming resistant to the effects of known modulators.

Antiviral activity is ascribed to a class of N(hydroxyethyl) pyrazole derivatives in U.S. Pat. No. 3,303,200. A number of pyrazoles are disclosed as reverse transcriptase inhibitors, including: a class of N-phenylpyrazoles (J. Med. Chem., 2000, 43, 1034); a class of C and S linked aryl pyrazoles (WO02/04424); and a class of O and S linked aryl pyrazoles, the O and S aryl link being adjacent to the nitrogen atom (WO02/30907).

According to the present invention there is provided a compound of formula (I)

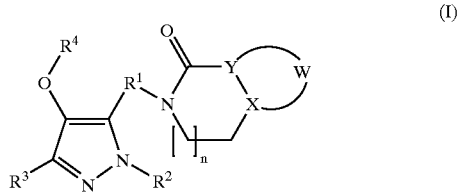

(I)

or a pharmaceutically acceptable salt, solvate or derivative thereof, wherein:

W—X—Y defines a five or six-membered partially saturated or aromatic ring containing 0 to 3 nitrogen atoms wherein X is CH or N and Y is CH or, when X is CH, may also be N; said ring being optionally substituted by halo, oxo, —CN, —$COR^5$, —$CONR^5R^5$, —$SO_2NR^5R^5$, —$NR^5SO_2R^5$, —$OR^5$, $OR^{11}$, —$NR^5R^5$, —($C_1$–$C_6$ alkylene)-$NR^5R^5$, $R^7$, $R^{11}$, or $CF_3$;

$R^1$ is $C_1$–$C_6$ alkylene;

$R^2$ is H, $C_1$–$C_6$ alkyl, $C_3$–$C_6$ alkenyl, $C_3$–$C_6$ alkynyl, $C_3$–$C_7$ cycloalkyl, $C_3$–$C_7$ cycloalkenyl, phenyl, benzyl, $R^8$ or $R^9$, said $C_1$–$C_6$ alkyl, $C_3$–$C_7$ cycloalkyl, phenyl and benzyl being optionally substituted by halo, —$OR^5$, —$OR^{10}$, —CN, —$CO_2R^7$, —$OCONR^5R^5$, —$CONR^5R^5$, —C(=$NR^5$)$NR^5OR^5$, —$CONR^5NR^5R^5$, —$NR^6R^6$, —$NR^5R^{10}$, —$NR^5COR^5$, —$NR^5COR^8$, —$NR^5COR^{10}$, —$NR^5CO_2R^5$, —$NR^5CONR^5R^5$, —$SO_2NR^5R^5$, —$NR^5SO_2R^5$, —$NR^5SO_2NR^5R^5$, $R^8$ or $R^9$;

$R^3$ is H, $C_1$–$C_6$ alkyl, $C_3$–$C_7$ cycloalkyl, phenyl, benzyl, halo, —CN, —$OR^7$, —$CO_2R^5$, —$CONR^5R^5$, $R^8$ or $R^9$, said $C_1$–$C_6$ alkyl, $C_3$–$C_7$ cycloalkyl, phenyl and benzyl being optionally substituted by halo, —CN, —$OR^5$, —$CO_2R^5$, —$CONR^5R^5$, —$OCONR^5R^5$, —$NR^5CO_2R^5$, —$NR^6R^6$, —$NR^5COR^5$, —$SO_2NR^5R^5$, —$NR^5CONR^5R^5$, —$NR^5SO_2R^5$, $R^8$ or $R^9$;

$R^4$ is phenyl, naphthyl or pyridyl, each being optionally substituted by $R^8$, halo, —CN, $C_1$–$C_6$ alkyl, $C_1$–$C_6$ haloalkyl, $C_3$–$C_7$ cycloalkyl, $C_1$–$C_6$ alkoxy, —$CONR^5R^5$, $OR^{11}$, $So_xR^6$, O—($C_1$–$C_6$ alkylene)-$CONR^5R^5$, O—($C_1$–$C_6$ alkylene)-$NR^5R^5$, or O—($C_1$–$C_6$ alkylene)—$OR^6$;

each $R^5$ is independently either H, $C_1$–$C_6$ alkyl or $C_3$–$C_7$ cycloalkyl or, when two $R^5$ groups are attached to the same nitrogen atom, those two groups taken together with the nitrogen atom to which they are attached represent azetidinyl, pyrrolidinyl, piperidinyl, homopiperidinyl, piperazinyl, homopiperazinyl or morpholinyl, said azetidinyl, pyrrolidinyl, piperidinyl, homopiperidinyl, piperazinyl, homopiperazinyl and morpholinyl being optionally substituted by $C_1$–$C_6$ alkyl or $C_3$–$C_7$ cycloalkyl;

each $R^6$ is independently either H, $C_1$–$C_6$ alkyl or $C_3$–$C_7$ cycloalkyl;

$R^7$ is $C_1$–$C_6$ alkyl or $C_3$–$C_7$ cycloalkyl;

$R^8$ is a five or six-membered, aromatic heterocyclic group containing (i) from 1 to 4 nitrogen heteroatom(s) or (ii) 1 or 2 nitrogen heteroatom(s) and 1 oxygen or 1 sulphur heteroatom or (iii) 1 or 2 oxygen or sulphur heteroatom(s), said heterocyclic group being optionally substituted by halo, oxo, —CN, —$COR^5$, —$CONR^5R^5$, —$SO_2NR^5R^5$, —$NR^5SO_2R^5$, —$OR^5$, —$NR^5R^5$, —($C_1$–$C_6$ alkylene)-$NR^5R^5$, $C_1$–$C_6$ alkyl, fluoro($C_1$–$C_6$)alkyl or $C_3$–$C_7$ cycloalkyl;

$R^9$ is a four to seven-membered, saturated or partially unsaturated heterocyclic group containing (i) 1 or 2 nitrogen heteroatom(s) or (ii) 1 nitrogen heteroatom and 1 oxygen or 1 sulphur heteroatom or (iii) 1 oxygen or sulphur heteroatom, said heterocyclic group being optionally substituted by oxo, $C_1$–$C_6$ alkyl, $C_3$–$C_7$ cycloalkyl, —$SO_2R^5$, —$CONR^5R^5$, —$COOR^5$, —CO—($C_1$–$C_6$ alkylene)-$OR^5$ or —$COR^5$ and optionally substituted on a carbon atom which is not adjacent to a heteroatom by halo, —$OR^5$, —$NR^5R^5$, —$NR^5COR^5$, —$NR^5COOR^5$, —$NR^5CONR^5R^5$, —$NR^5SO_2R^5$ or —CN;

$R^{10}$ is $C_1$–$C_6$ alkyl substituted by $R^8$, $R^9$, —$OR^5$, —$CONR^5R^5$, —$NR^5COR^5$ or —$NR^5R^5$;

$R^{11}$ is phenyl optionally substituted by halo, —CN, —$COR^5$, —$CONR^5R^5$, —$SO_2NR^5R^5$, —$NR^5SO_2R^5$, —$OR^5$, —$NR^5R^5$, —($C_1$–$C_6$ alkylene)-$NR^5R^5$, $C_1$–$C_6$ alkyl, halo($C_1$–$C_6$)alkyl or $C_3$–$C_7$ cycloalkyl; and x and n are independently 0, 1 or 2.

In the above definitions, halo means fluoro, chloro, bromo or iodo. Unless otherwise stated, alkyl, alkenyl, alkynyl, alkylene and alkoxy groups containing the requisite number of carbon atoms can be unbranched or branched chain. Examples of alkyl include methyl, ethyl, n-propyl, i-propyl, n-butyl, i-butyl, sec-butyl and t-butyl. Examples of alkenyl include ethenyl, propen-1-yl, propen-2-yl, propen-3-yl, 1-buten-1-yl, 1-buten-2-yl, 1-buten-3-yl, 1-buten-4-yl, 2-buten-1-yl, 2-buten-2-yl, 2-methylpropen-1-yl or 2-methylpropen-3-yl. Examples of alkynyl include ethynyl, propyn-1-yl, propyn-3-yl, 1-butyn-1-yl, 1-butyn-3-yl, 1-butyn4-yl, 2-butyn-1-yl. Examples of alkylene include methylene, 1,1-ethylene, 1,2-ethylene, 1,1-propylene, 1,2-propylene, 2,2-propylene and 1,3-propylene. Examples of alkoxy include methoxy, ethoxy, n-propoxy, i-propoxy, n-butoxy, i-butoxy, sec-butoxy and t-butoxy. Examples of cycloalkyl include cyclopropyl, cyclobutyl, cyclopentyl, cyclohexyl and cycloheptyl. Where a heterocyclic group $R^8$ or $R^9$ is attached to an oxygen, sulphur or nitrogen heteroatom the heterocyclic group $R^8$ or $R^9$ must be linked through a ring carbon atom.

The pharmaceutically acceptable salts of the compounds of formula (I) include the acid addition and the base salts thereof.

Suitable acid addition salts are formed from acids which form non-toxic salts and examples are the hydrochloride, hydrobromide, hydroiodide, chloride, bromide, iodide, sulphate, bisulphate, nitrate, phosphate, hydrogen phosphate, acetate, fumarate, pamoate, aspartate, besylate, carbonate, bicarbonate/, camsylate, D and L-lactate, D and L-tartrate, esylate, mesylate, malonate, orotate, gluceptate, methylsulphate, stearate, glucuronate, 2-napsylate, tosylate, hibenzate, nicotinate, isethionate, malate, maleate, citrate, gluconate, succinate, saccharate, benzoate, esylate, and pamoate salts.

Suitable base salts are formed from bases which form non-toxic salts and examples are the sodium, potassium, aluminium, calcium, magnesium, zinc, choline, diolamine, olamine, arginine, glycine, tromethamine, benzathine, lysine, meglumine and diethylamine salts.

For reviews on suitable salts see Berge et al, J. Pharm. Sci., 66, 1–19, 1977 and Bighley et al, Encyclopedia of Pharmaceutical Technology, Marcel Dekker Inc, New York, 1996, Vol 13, pp453–497

The pharmaceutically acceptable solvates of the compounds of formula (I) include the hydrates thereof.

The compound of formula (I) may be modified to provide pharmaceutically acceptable derivatives thereof at any of the functional groups in the compound. Examples of such derivatives are described in: Drugs of Today, Volume 19, Number 9, 1983, pp 499–538; Topics in Chemistry, Chapter 31, pp 306–316; and in "Design of Prodrugs" by H. Bundgaard, Elsevier, 1985, Chapter 1 (the disclosures in which documents are incorporated herein by reference) and include: esters, carbonate esters, hemi-esters, phosphate esters, nitro esters, sulfate esters, sulfoxides, amides, sulphonamides, carbamates, azo-compounds, phosphamides, glycosides, ethers, acetals and ketals.

The invention encompasses all isomers of the compound of formula (I) and pharmaceutically acceptable salts, solvates or derivatives thereof, including all geometric, tautomeric and optical forms, and mixtures thereof (e.g. racemic mixtures).

Separation of diastereoisomers may be achieved by conventional techniques, e.g. by fractional crystallisation, chromatography or high performance liquid chromatography (HPLC) of a stereoisomeric mixture of compounds. An individual enantiomer of a compound may also be prepared from a corresponding optically pure intermediate or by resolution, such as by HPLC of the corresponding racemate using a suitable chiral support, or by fractional crystallisation of the diastereoisomeric salts formed by reaction of the corresponding racemate with a suitable optically active acid or base, as appropriate.

The compound of formula (I) and pharmaceutically acceptable salts, solvates or derivatives thereof may have the ability to crystallize in more than one form, a characteristic known as polymorphism, and all such polymorphic forms ("polymorphs") are encompassed within the scope of the invention. Polymorphism generally can occur as a response to changes in temperature or pressure or both, and can also result from variations in the crystallization process. Polymorphs can be distinguished by various physical characteristics, and typically the x-ray diffraction patterns, solubility behaviour, and melting point of the compound are used to distinguish polymorphs.

Compounds of formula (I), pharmaceutically acceptable salts, solvates and derivatives thereof, isomers thereof, and polymorphs thereof, are hereinafter referred to as the compounds of the invention.

Preferred compounds of the invention are the compounds of formula (I) and pharmaceutically acceptable salts and solvates thereof.

Preferably, W—X—Y defines a five or six-membered partially saturated or aromatic ring containing 0 to 2 nitrogen atoms wherein X is CH or N and Y is CH or, when X is CH, may also be N; said ring being optionally substituted by halo, oxo, —CN, —OR$^5$, —NR$^5$R$^5$, —(C$_1$–C$_6$ alkylene)-NR$^5$R$^5$, R$^7$, or CF$_3$.

Preferably, W—X—Y defines a five or six-membered partially saturated or aromatic ring containing 0 to 2 nitrogen atoms wherein X is CH or N and Y is CH or, when X is CH, may also be N; said ring being optionally substituted by oxo, —CN, —C$_1$–C$_6$ alkoxy, —NH$_2$, —N(C$_1$–C$_6$ alkyl)(C$_1$–C$_6$ alkyl), C$_1$–C$_6$ alkyl, or CF$_3$.

Preferably, W—X—Y defines a phenyl or pyridyl ring, and said ring being optionally substituted by —CN.

Preferably, R$^1$ is methylene, ethylene or propylene.

Preferably, R$^1$ is methylene.

Preferably, R$^2$ is H, C$_1$–C$_6$ alkyl, C$_3$–C$_6$ alkenyl, phenyl, benzyl or R$^9$, said phenyl, benzyl or C$_1$–C$_6$ alkyl being optionally substituted by halo, —OR$^5$, —OR$^{10}$, —CN, —CO$_2$R$^7$, —OCONR$^5$R$^5$, —CONR$^5$R$^5$, —C(=NR$^5$)NR$^5$OR$^5$, —CONR$^5$NR$^5$R$^5$, —NR$^6$R$^6$, —NR$^5$R$^{12}$, —NR$^5$COR$^5$, —NR$^5$COR$^8$, —NR$^5$COR$^{12}$, —NR$^5$CO$_2$R$^5$, —NR$^5$CONR$^5$R$^5$, —SO$_2$NR$^5$R$^5$, —NR$^5$SO$_2$R$^5$, R$^8$ or R$^9$.

Preferably, R$^2$ is H, C$_1$–C$_6$ alkyl, phenyl or benzyl, said C$_1$–C$_6$ alkyl being optionally substituted by halo, —OR$^5$, —OR$^{10}$ or —CN.

Preferably, R$^2$ is H or C$_1$–C$_3$ alkyl.

Preferably, R$^2$ is H.

Preferably, R$^3$ is H, C$_1$–C$_6$ alkyl or C$_3$–C$_7$ cycloalkyl, said C$_1$–C$_6$ alkyl being optionally substituted by halo, —CN, —OR$^5$, —CO$_2$R$^5$, —CONR$^5$R$^5$, —OCONR$^5$R$^5$, —NR$^5$CO$_2$R$^5$, —NR$^6$R$^6$, —NR$^5$COR$^5$, —SO$_2$NR$^5$R$^5$, —NR$^5$CONR$^5$R$^5$, —NR$^5$SO$_2$R$^5$, R$^8$ or R$^9$.

Preferably, R$^3$ is H or C$_1$–C$_6$ alkyl.

Preferably, R$^3$ is H or C$_1$–C$_4$ alkyl.

Preferably, R$^3$ is methyl or ethyl.

Preferably, R$^4$ is phenyl optionally substituted by R$^8$, halo, —CN, C$_1$–C$_6$ alkyl, C$_1$–C$_6$ haloalkyl, C$_3$–C$_7$ cycloalkyl or C$_1$–C$_6$ alkoxy.

Preferably, R$^4$ is phenyl substituted by R$^8$, halo, —CN, C$_1$–C$_6$ alkyl, or C$_1$–C$_6$ alkoxy.

Preferably, R$^4$ is phenyl substituted by halo or —CN.

Preferably, R$^4$ is phenyl substituted by chloro or —CN.

Preferably, R$^4$ is 3,5-dicyanophenyl or 3-chloro-5-cyanophenyl.

Preferably, R$^8$ is pyrrolyl, imidazolyl, pyrazolyl, 1,2,3-triazolyl, 1,2,4-triazolyl, tetrazolyl, oxazolyl, isoxazolyl, thiazolyl, isothiazolyl, 1,2,4-oxadiazolyl, 1,3,4-oxadiazolyl, furanyl, thienyl, pyridinyl, pyridazinyl, pyrimidinyl or pyrazinyl, each being optionally substituted by halo, —CN, —COR$^5$, —CONR$^5$R$^5$, —SO$_2$NR$^5$R$^5$, —NR$^5$SO$_2$R$^5$, —OR$^5$, —NR$^5$R$^5$, —(C$_1$–C$_6$ alkylene)-NR$^5$R$^5$, —(C$_1$–C$_6$ alkyl, fluoro(C$_1$–C$_6$)alkyl or C$_3$–C$_7$ cycloalkyl.

Preferably, R$^8$ is imidazolyl, pyrazolyl, 1,2,4-triazolyl, 1,2,4-oxadiazolyl, 1,3,4-oxadiazolyl, pyridinyl, pyrazinyl or pyrimidinyl, each being optionally substituted by halo, —CN, —COR$^5$, —CONR$^5$R$^5$, —SO$_2$NR$^5$R$^5$, —NR$^5$SO$_2$R$^5$, —OR$^5$, —NR$^5$R$^5$, —(C$_1$–C$_6$ alkylene)-NR$^5$R$^5$, C$_1$C$_6$ alkyl, fluoro(C$_1$–C$_6$)alkyl or C$_3$–C$_7$ cycloalkyl.

Preferably, R$^8$ is imidazolyl, pyrazolyl, 1,2,4-trazolyl, 1,2,4-oxadiazolyl, 1,3,4-oxadiazolyl, pyridinyl, pyrazinyl or pyrimidinyl, each being optionally substituted by —OR$^5$, —NR$^5$R$^5$ or C$_1$–C$_6$ alkyl.

Preferably, R$^8$ is imidazolyl, pyrazolyl, 1,2,4-triazolyl, 1,2,4-oxadiazolyl, 1,3,4-oxadiazolyl, pyridinyl, pyrazinyl or pyrimidinyl, each being optionally substituted by —OH, —NH$_2$ or methyl.

Preferably, R$^9$ is azetidinyl, tetrahydropyrrolyl, piperidinyl, azepinyl, oxetanyl, tetrahydrofuranyl, tetrahydropyranyl, oxepinyl, morpholinyl, piperazinyl or diazepinyl, each being optionally substituted by oxo, C$_1$–C$_6$ alkyl, C$_3$–C$_7$ cycloalkyl, —SO$_2$R$^5$, —CONR$^5$R$^6$, —COOR$^5$, —CO—(C$_1$–C$_6$ alkylene)-OR$^5$ or —COR$^5$ and optionally substituted on a carbon atom which is not adjacent to a heteroatom by halo, —OR$^5$, —NR$^5$R$^5$, —NR$^5$COR$^5$, —NR$^5$COOR$^5$, —NR$^5$CONR$^5$R$^5$, —NR$^5$SO$_2$R$^5$ or —CN.

Preferably, R$^9$ is azetidinyl, piperidinyl, tetrahydrofuranyl, piperazinyl or morpholinyl, each being optionally substituted by oxo, C$_1$–C$_6$ alkyl, C$_3$–C$_7$ cycloalkyl, —SO$_2$R$^5$, —CONR$^5$R$^5$, —COOR$^5$, —CO—(C$_1$–C$_6$ alkylene)-OR$^5$ or —COR$^5$ and optionally substituted on a carbon atom which is not adjacent to a heteroatom by halo, —OR$^5$, —NR$^5$R$^5$, —NR$^5$COR$^5$, —NR$^5$COOR$^5$, —NR$^5$CONR$^5$R$^5$, —NR$^5$SO$_2$R$^5$ or —CN.

Preferably, $R^9$ is azetidinyl, piperidinyl, tetrahydrofuranyl, piperazinyl or morpholinyl, each being optionally substituted by $C_1$–$C_6$ alkyl, —$SO_2R^5$, —$CONR^5R^5$, —$COOR^5$, —CO—($C_1$–$C_6$ alkylene)-$OR^5$ or —$COR^5$ and optionally substituted on a carbon atom which is not adjacent to a heteroatom by —$OR^5$ or —$NR^5COR^5$.

Preferably, $R^9$ is azetidinyl, piperidinyl, tetrahydrofuranyl, piperazinyl or morpholinyl, each being optionally substituted by —$CH_3$, —$SO_2CH_3$, —$CONH_2$, —$COOCH_3$, —$COCH_2OCH_3$ or —$COCH_3$ and optionally substituted on a carbon atom which is not adjacent to a heteroatom by —$OCH_3$ or —$NHCOCH_3$.

Preferably, $R^{10}$ is $C_1$–$C_4$ alkyl substituted by $R^8$, $R^9$, —$OR^5$, —$CONR^5R^5$, —$NR^5COR^5$ or —$NR^5R^5$.

Preferably, $R^{10}$ is $C_1$–$C_4$ alkyl substituted by $R^9$, —$OR^5$, —$NR^5COR^5$ or —$NR^5R^5$.

Preferably, $R^{10}$ is $C_1$–$C_2$ alkyl substituted by tetrahydrofuranyl, —$OCH_3$, —$NHCOCH_3$ or —$NH_2$.

Preferably, $R^{11}$ is phenyl substituted by halo, —CN, —$COR^5$, —$CONR^5R^5$, —$SO_2NR^5R^5$, —$NR^5SO_2R^5$, —$OR^5$, —$NR^5R^5$, —($C_1$–$C_6$ alkylene)-$NR^5R^5$, $C_1$–$C_6$ alkyl, halo($C_1$–$C_6$)alkyl or $C_3$–$C_7$ cycloalkyl.

Preferably, $R^{11}$ is phenyl substituted by halo, —CN, —$CONR^5R^5$, —$SO_2NR^5R^5$ or —$OR^5$.

Preferably, $R^{11}$ is phenyl substituted by fluoro, —CN, —$CONH_2$, —$SO_2NH_2$ or —$OCH_3$.

Preferably, n is 0 or 1.

Preferably, n is 0.

Preferred groups of compounds according to the invention include all combinations of the preferred definitions for individual substituents given above.

Preferred compounds of the invention are:

3-chloro-5-[3-methyl-5-(1-oxo-1,3-dihydro-isoindol-2ylmethyl)-1H-pyrazol-4-yloxy]-benzonitrile;

5-[3-methyl-5-(1-oxo-1,3-dihydro-isoindol-2-ylmethyl)-1H-pyrazol-4-yloxy]-isophthalonitrile;

and pharmaceutically acceptable salts, solvates or derivatives thereof.

The compounds of the invention may have advantages over those of the prior art with regard to a number of useful properties or combinations thereof, such as potency, duration of action, pharmacokinetics, spectrum of activity, side effect profile, solubility, chemical stability, and so on.

The compounds of the invention may be prepared by any method known in the art for the preparation of compounds of analogous structure. The compounds of the invention can be prepared by the procedures described in the methods below, or by the specific methods described in the Examples, or by similar methods to either. The invention also encompasses any one or more of these processes for preparing the compounds of the invention, in addition to any novel intermediates used therein.

In the following methods, W, X, Y, $R^1$ to $R^4$, and n are as previously defined for a compound of formula (I), unless otherwise stated; Z is H or $C_1$–$C_4$ alkoxy (e.g. methoxy); THF is tetrahydrofuran; DCM is dichloromethane; DMF is N,N-dimethylformamide and Ac is acyl.

Compounds of formula (I) may be prepared according to Scheme 1 that follows.

According to Scheme 1, compounds of formula (I) may be prepared by the reaction of a compound of formula (II) with an amine of formula (IV) under conventional conditions. For aldehydes of formula (II), i.e. wherein Z is H, reaction conditions are those of reductive amination/alkylation in the presence of a reducing agent. For esters of formula (II), i.e. wherein Z is $C_1$–$C_4$ alkoxy (e.g. methoxy), reaction conditions are those of alkylation/condensation in the presence of a base.

Scheme 1

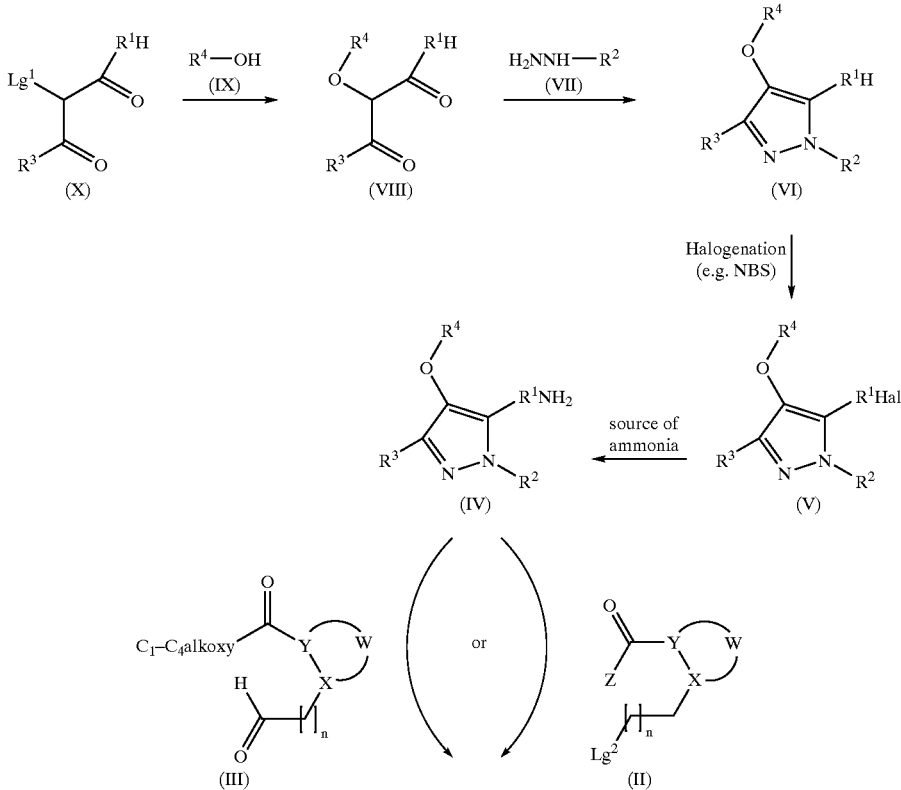

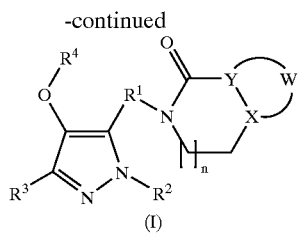

(I)

Conveniently, reductive amination/alkylation is effected using a hydride reducing agent, such as a borohydride (e.g. Na(OAc)$_3$BH or NaCNBH$_3$); optionally, an activating agent, such as acetic acid or sodium acetate; in the presence of a solvent, such as an ether (e.g. THF) or a haloalkane (e.g. DCM); and at ambient to elevated temperature, such as ambient temperature.

Conveniently, alkylation/condensation is effected using an alkali metal base, such as an alkali metal carbonate (e.g. sodium, potassium or caesium carbonate); in the presence of a solvent, such as a polar aprotic solvent (e.g. acetonitrile or DMF); and at ambient to elevated temperature, such as ambient temperature to 40° C.

Amines of formula (IV) may be prepared by reaction of the corresponding halide of formula (V) with a source of ammonia under conventional conditions. Conveniently the reaction is effected in the presence a solvent, such as an alcohol (e.g. ethanol or isopropanol), said solvent being saturated with ammonia; and at reduced to ambient to elevated temperature, such as reduced temperature (e.g. 0° C.).

Compounds of formula (V) may be prepared by halogenation of a compound of formula (VI) using a source of halogen, such as a molecular halogen (e.g. bromine) or an N-halo-succinimide (e.g. N-bromo-succinimide), under conventional conditions. Conveniently the halogenation is effected in the presence of a solvent, such as a haloalkane (e.g. carbon tetrachloride or 1,1,1-trichloroethane); optionally a radical initiation catalyst, such as ultraviolet light or AIBN; and at ambient to elevated temperature, such as under reflux.

Compounds of formula (VI) may be prepared by the reaction of a compound of formula (VIII) with a hydrazine of formula (VII), or a salt or hydrate thereof. Conveniently, the reaction is effected a solvent, such as a protic solvent (e.g. acetic acid); at ambient to elevated temperature, such as ambient temperature; and optionally in the presence of an acid (e.g. acetic acid) or a base, such as a tertiary amine (e.g. triethylamine).

Compounds of formula (VIII) may be prepared by the reaction of a compound of formula (X) with an alcohol of formula (IX). Conveniently, the reaction is effected in the presence of a solvent, such as a polar solvent (e.g. acetone); a base, such as an inorganic base, preferably a metal carbonate (e.g. potassium or caesium carbonate); optionally, a nucleophilic catalyst, such as sodium iodide or tetrabutylammonium iodide; and at ambient to elevated temperature, such as elevated temperature (e.g. under reflux).

Ketoesters of formula (IX) are either commercially available, known in the literature, or may be prepared by conventional methods (e.g., where Lg$^1$ is Cl, by the chlorination of corresponding ketoesters, for instance using sulphonyl chloride).

Compounds of formula (I) may also be prepared by reaction of a compound of formula (III) with an amine of formula (IV) under conventional conditions. Conveniently, the reaction is effected in the presence of a reducing agent under conditions of reductive amination/alkylation, such as those described above for the preparation of a compound of formula (I) by reaction of a compound of formula (II) with an amine of formula (IV).

Compounds of formula (I) in which R$^3$ is halo can be prepared from a compound of formula (XI)

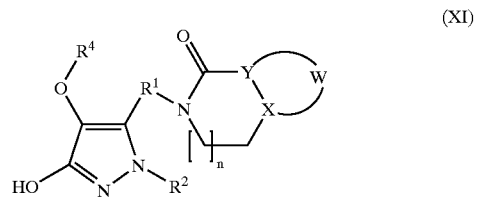

(XI)

under conventional conditions. Conveniently, the reaction is effected by an inorganic acid halide, such as an inorganic acid chloride (e.g. POCl$_3$); optionally in the presence of a solvent, such as a polar aprotic solvent (e.g. N,N-dimethylformamide); and at reduced to ambient temperature, such as ambient temperature.

Compounds of formula (XI) may be prepared using the routes described above, mutatis mutandis.

It will be appreciated by those skilled in the art that, in many cases, compounds of formula (I) may be converted into other compounds of formula (I) by functional group transformations, including for example the following interconversions.

Compounds of formula (I) in which R$^2$ is optionally substituted C$_1$–C$_6$ alkyl may be prepared from compounds of formula (I) in R$^2$ is H by reaction with an alkylating agent. Suitable alkylating agents include bromoacetonitrile, ethyl 4-chloroacetoacetate, methyl bromoacetate and chloroethylamine hydrochloride. Conveniently, alkylation is effected in the presence of a suitable solvent, such as an alcohol (e.g. ethanol) or a polar aprotic solvent (e.g. N,N-dimethylformamide); a base, such as a metal hydride (e.g. sodium hydride) or metal alkoxide (e.g. sodium ethoxide); and at ambient to elevated temperature, such as under reflux.

Compounds of formula (I) in which R$^2$ or R$^3$ contains a hydroxy group may be prepared from the corresponding compound of formula (I) in which R$^2$ or R$^3$ contains an ester group by reduction. Conveniently, the reduction is effected by a metal hydride agent, such as lithium aluminium hydride; in a solvent, such as an ether (e.g. diethyl ether); and at reduced temperature, such as from −78° C. to 0° C.

Compounds of formula (I) in which R$^2$ or R$^3$ are substituted by a heterocycle of formula R$^8$ and R$^9$ may be prepared by standard heterocycle-forming reactions well known to the skilled man (see, for example, Advanced Organic Chemistry, 3rd Edition, by Gerry March or Comprehensive Heterocyclic Chemistry, A. R. Katritzky, C. W. Rees, E. F. V. Scriven, Volumes 1–11).

Compounds of formula (I) in which R$^3$ is —CO$_2$H may be prepared by hydrolysis of a corresponding compound of formula (I) in which R$^3$ is —CO$_2$R$^5$. Conveniently, the reaction is effected in the presence of a solvent, such as an alcohol (e.g. aqueous ethanol), or an ether (e.g. aqueous 1,4-dioxan); and in the presence of a base, such as a metal hydroxide (e.g. sodium hydroxide). The skilled artisan will appreciate that such an acid may be converted into a primary amide by reaction with ammonia and a suitable coupling agent, such as a carbodiimide, e.g. dicyclohexylcarbodiimide, and that such a primary amide may then be converted into a nitrile by dehydration with a suitable dehydrating agent, such as phosphoryl chloride.

Compounds of formula (I) in which $R^3$ is $C_1$–$C_6$ alkyl may be converted into the compounds of formula (I) in which $R^3$ is $C_1$–$C_6$ alkyl substituted by halo (such as bromo), by halogenation, using a suitable halogenating agent. Conveniently the reaction is effected in the presence of a solvent, such as a haloalkane (e.g. dichloromethane) and at ambient temperature. Suitable halogenating agents include halogens (e.g. bromine) or N-halosuccinimides (e.g. N-bromsuccinimide).

Compounds of formula (I) containing an —OH, —NH— or —$NH_2$ group may be prepared by the deprotection of the corresponding compound bearing an —$OP^1$, —$NP^1$- or —$NHP^1$ group, respectively, wherein the group $P^1$ is a suitable protecting group. Examples of suitable protecting groups will be apparent to the skilled person; see, for instance, 'Protecting groups in Organic Synthesis (Second Edition)' by Theodora W. Green and Peter G. M. Wuts, 1991, John Wiley and Sons. Such compounds bearing an —$OP^1$, —$NP^1$- or —$NHP^1$ group may be prepared using the routes described above, mutatis mutandis.

Compounds of formulae (II), (III), (VII) and (IX) are either commercially available, known in the literature or easily prepared by methods well known to those skilled in the art, such as those described in the Preparations hereinafter.

The compounds of the invention can be administered alone, but will generally be administered in admixture with a suitable pharmaceutical excipient, diluent or carrier selected with regard to the intended route of administration and standard pharmaceutical practice.

For example, the compounds of the invention can be administered orally, buccally or sublingually in the form of tablets, capsules, multi-particulates, gels, films, ovules, elixirs, solutions or suspensions, which may contain flavouring or colouring agents, for immediate-, delayed-, modified-, sustained-, pulsed- or controlled-release applications. The compounds of the invention may also be administered as fast-dispersing or fast-dissolving dosage forms or in the form of a high energy dispersion or as coated particles. Suitable formulations of the compounds of the invention may be in coated or uncoated form, as desired.

Such solid pharmaceutical compositions, for example, tablets, may contain excipients such as microcrystalline cellulose, lactose, sodium citrate, calcium carbonate, dibasic calcium phosphate, glycine and starch (preferably corn, potato or tapioca starch), disintegrants such as sodium starch glycollate, croscarmellose sodium and certain complex silicates, and granulation binders such as polyvinylpyrrolidone, hydroxypropylmethylcellulose (HPMC), hydroxypropylcellulose (HPC), sucrose, gelatin and acacia. Additionally, lubricating agents such as magnesium stearate, stearic acid, glyceryl behenate and talc may be included.

GENERAL EXAMPLE

A formulation of the tablet could typically contain from 0.01 mg to 500 mg of active compound whilst tablet fill weights may range from 50 mg to 1000 mg. An example of a formulation for a 10 mg tablet is illustrated below:

| Ingredient | % w/w |
|---|---|
| Compound of the invention | 10.000* |
| Lactose | 64.125 |
| Starch | 21.375 |
| Croscarmellose sodium | 3.000 |
| Magnesium Stearate | 1.500 |

*Quantity adjusted in accordance with drug activity.

The tablets are manufactured by a standard process, for example, direct compression or a wet or dry granulation process. The tablet cores may be coated with appropriate overcoats.

Solid compositions of a similar type may also be employed as fillers in gelatin or HPMC capsules. Preferred excipients in this regard include lactose, starch, a cellulose, milk sugar or high molecular weight polyethylene glycols. For aqueous suspensions and/or elixirs, the compounds of the invention may be combined with various sweetening or flavouring agents, colouring matter or dyes, with emulsifying and/or suspending agents and with diluents such as water, ethanol, propylene glycol and glycerin, and combinations thereof.

The compounds of the invention can also be administered parenterally, for example, intravenously, intra-arterially, intraperitoneally, intrathecally, intraventricularly, intraurethrally, intrasternally, intracranially, intramuscularly or subcutaneously, or they may be administered by infusion or needleless injection techniques. For such parenteral administration they are best used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well-known to those skilled in the art.

For oral and parenteral administration to human patients, the daily dosage level of the compounds of the invention will usually be from 0.01 to 30 mg/kg, preferably from 0.01 to 5 mg/kg (in single or divided doses).

Thus tablets or capsules of the compound of the invention may contain from 1 to 500 mg of active compound for administration singly or two or more at a time, as appropriate. The physician in any event will determine the actual dosage which will be most suitable for any individual patient and it will vary with the age, weight and response of the particular patient. The above dosages are exemplary of the average case. There can, of course, be individual instances where higher or lower dosage ranges are merited and such are within the scope of this invention. The skilled person will appreciate that, in the treatment of certain conditions the compounds of the invention may be taken as a single dose as needed or desired.

The compounds of invention can also be administered intranasally or by inhalation and are conveniently delivered in the form of a dry powder inhaler or an aerosol spray presentation from a pressurised container, pump, spray, atomiser or nebuliser, with or without the use of a suitable propellant, e.g. dichlorodifluoromethane, trichlorofluoromethane, dichlorotetrafluoroethane, a hydrofluoroalkane such as 1,1,1,2-tetrafluoroethane (HFA 134A [trade mark]) or 1,1,1,2,3,3,3-heptafluoropropane (HFA 227EA [trade mark]), carbon dioxide or other suitable gas. In the case of a pressurised aerosol, the dosage unit may be determined by providing a valve to deliver a metered amount. The pressurised container, pump, spray, atomiser or nebuliser may contain a solution or suspension of the active compound, e.g. using a mixture of ethanol and the propellant as the solvent, which may additionally contain a lubricant, e.g. sorbitan trioleate. Capsules and cartridges (made, for example, from gelatin) for use in an inhaler or insufflator may be formulated to contain a powder mix of a compound of the invention and a suitable powder base such as lactose or starch.

Alternatively, the compounds of the invention can be administered in the form of a suppository or pessary, or they may be applied topically in the form of a gel, hydrogel, lotion, solution, cream, ointment or dusting powder. The compounds of the invention may also be dermally or transdermally administered, for example, by the use of a skin patch. They may also be administered by the pulmonary or rectal routes.

They may also be administered by the ocular route. For ophthalmic use, the compounds can be formulated as micronised suspensions in isotonic, pH adjusted, sterile saline, or, preferably, as solutions in isotonic, pH adjusted, sterile saline, optionally in combination with a preservative such as a benzylalkonium chloride. Alternatively, they may be formulated in an ointment such as petrolatum.

For application topically to the skin, the compounds of the invention can be formulated as a suitable ointment containing the active compound suspended or dissolved in, for example, a mixture with one or more of the following: mineral oil, liquid petrolatum, white petrolatum, propylene glycol, polyoxyethylene polyoxypropylene compound, emulsifying wax and water. Alternatively, they can be formulated as a suitable lotion or cream, suspended or dissolved in, for example, a mixture of one or more of the following: mineral oil, sorbitan monostearate, a polyethylene glycol, liquid paraffin, polysorbate 60, cetyl esters wax, cetearyl alcohol, 2-octyldodecanol, benzyl alcohol and water.

The compounds of the invention may also be used in combination with a cyclodextrin. Cyclodextrins are known to form inclusion and non-inclusion complexes with drug molecules. Formation of a drug-cyclodextrin complex may modify the solubility, dissolution rate, bioavailability and/or stability property of a drug molecule. Drug-cyclodextrin complexes are generally useful for most dosage forms and administration routes. As an alternative to direct complexation with the drug the cyclodextrin may be used as an auxiliary additive, e.g. as a carrier, diluent or solubiliser. Alpha-, beta- and gamma-cyclodextrins are most commonly used and suitable examples are described in WO91/11172, WO94/02518 and WO98/55148.

It is to be appreciated that all references herein to treatment include curative, palliative and prophylactic treatment.

Oral administration is preferred.

Included within the scope of the invention are embodiments comprising the co-administration of a compound of the invention with one or more additional therapeutic agents, and compositions containing a compound of the invention along with one or more additional therapeutic agents. Such a combination therapy is especially useful for the prevention and/or treatment of infection by HIV and related retroviruses which may evolve rapidly into strains resistant to any monotherapy. Alternatively, additional therapeutic agents may be desirable to treat diseases and conditions which result from or accompany the disease being treated with the compound of the invention. For example, in the treatment of an HIV or related retroviral infection, it may be desirable to additionally treat opportunistic infections, neoplasms and other conditions which occur as a result of the immunocompromised state of the patient being treated.

Preferred combinations of the invention include simultaneous or sequential treatment with a compound of the invention and one or more:

(a) reverse transcriptase inhibitors such as abacavir, adefovir, didanosine, lamivudine, stavudine, zalcitabine and zidovudine;
(b) non-nucleoside reverse transcriptase inhibitors such as capavirine, delavirdine, efavirenz, and nevirapine;
(c) HIV protease inhibitors such as indinivir, nelfinavir, ritonavir, and saquinavir;
(d) CCR5 antagonists such as TAK-779 or UK-427,857;
(e) CXCR4 antagonists such as AMD-3100;
(f) integrase inhibitors, such as L-870,810 or S-1360;
(g) inhibitors of viral fusion such as T-20;
(h) investigational drugs such as trizivir, KNI-272, amprenavir, GW-33908, FTC, PMPA, MKC-442, MSC-204, MSH-372, DMP450, PNU-140690, ABT-378, KNI-764, DPC-083, TMC-120 or TMC-125;
(i) antifungal agents, such as fluconazole, itraconazole or voriconazole; or
(j) antibacterial agents, such as azithromycin.

The activity of the compounds of the invention as reverse transcriptase inhibitors may be measured using the following assay.

Inhibition of HIV-1 Reverse Transcriptase Enzyme

Using purified recombinant HIV-1 reverse transcriptase (RT, EC, 2.7.7.49) obtained by expression in *Escherichia Coli*, a 96-well plate assay system is established for assaying a large number of samples using either the Poly(rA)-oligo (dT) Reverse Transcriptase [3H]-SPA enzyme assay system (Amersham NK9020) or the [3H]-flashplate enzyme assay system (NEN—SMP 103) and following the manufacturer's recommendations. The compounds are dissolved in 100% DMSO and diluted with the appropriate buffer to a 5% final DMSO concentration. The inhibitory activity is expressed in percent inhibition relative to DMSO control. The concentration at which compound inhibits reverse transcriptase by 50% is expressed as the $IC_{50}$ of the compound.

The compounds of Examples 1 and 4, when tested according to the above procedure, had $IC_{50}$ values of, respectively, 76 and 505 nanomolar.

Thus the invention provides:

(i) a compound of formula (I) or a pharmaceutically acceptable salt, solvate or derivative thereof;
(ii) a process for the preparation of a compound of formula (I) or a pharmaceutically acceptable salt, solvate or derivative thereof;
(iii) a pharmaceutical composition including a compound of formula (I) or a pharmaceutically acceptable salt, solvate or derivative thereof, together with a pharmaceutically acceptable excipient, diluent or carrier;
(iv) a compound of formula (I) or a pharmaceutically acceptable salt, solvate or composition thereof, for use as a medicament;
(v) a compound of formula (I) or a pharmaceutically acceptable salt, solvate or composition thereof, for use as a reverse transcriptase inhibitor or modulator;
(vi) a compound of formula (I) or a pharmaceutically acceptable salt, solvate or composition thereof, for use in the treatment of an HIV or genetically-related retroviral infection, or a resulting acquired immune deficiency syndrome (AIDS);
(vii) a use of the compound of formula (I) or of a pharmaceutically acceptable salt, solvate or composition thereof, for the manufacture of a medicament having reverse transcriptase inhibitory or modulating activity;
(viii) the use of a compound of formula (I) or of a pharmaceutically acceptable salt, solvate or composition thereof, for the manufacture of a medicament for the treatment of an HIV or genetically-related retroviral infection, or a resulting acquired immune deficiency syndrome (AIDS);

(ix) a method of treating an HIV or a genetically-related retroviral infection, or a resulting acquired immune deficiency syndrome (AIDS), comprising administering an effective amount of a compound of formula (I) or a pharmaceutically acceptable salt, solvate or composition thereof; and (xi) certain novel intermediates disclosed herein.

The following Examples illustrate the preparation of the compounds of formula (I). The synthesis of certain intermediates used therein are described in the Preparations section that follows the Examples.

$^1$H Nuclear magnetic resonance (NMR) spectra were in all cases consistent with the proposed structures. Characteristic chemical shifts (δ) are given in parts-per-million downfield from tetramethylsilane using conventional abbreviations for designation of major peaks: e.g. s, singlet; d, doublet; t, triplet; q, quartet; m, multiplet; br, broad. The following abbreviations have been used: HRMS, high resolution mass spectrometry; hplc, high performance liquid chromatography; nOe, nuclear Overhauser effect; m.p., melting point; CDCl$_3$, deuterochloroform; D$_6$-DMSO, deuterodimethylsulphoxide; CD$_3$OD, deuteromethanol. Where thin layer chromatography (TLC) has been used it refers to silica gel TLC using silica gel 60 F$_{254}$ plates, R$_f$ is the distance travelled by a compound divided by the distance travelled by the solvent front on a TLC plate.

Example 1

3-Chloro-5-[3-methyl-5-(1-oxo-1,3-dihydro-isoindol-2ylmethyl)-1H-pyrazol-4-yloxy]-benzonitrile

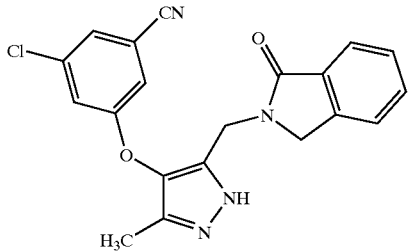

Sodium triacetoxyborohydride (93 mg, 0.44 mmol) was added to a solution of the amine of preparation 13 (107 mg, 0.4 mmol), methyl 2-formylbenzoate (Maybridge) (67 mg, 0.41 mmol) and acetic acid (23 μl, 0.4 mmol) in dichloromethane (2 ml), and the reaction stirred at room temperature for 1 hour. The mixture was diluted with dichloromethane (20 ml), and washed with sodium bicarbonate solution (10 ml). This aqueous solution was extracted with dichloromethane (2×10 ml), and the combined organic solutions were washed with brine (10 ml), dried over magnesium sulphate and evaporated under reduced pressure. The crude product was purified by chromatography on silica gel using an elution gradient of dichloromethane:methanol:0.88 ammonia (100:0:0 to 95:5:0.5) to afford the title compound as a white solid.

$^1$H NMR (400 MHz, DMSO-d$_6$): δ 2.03 (s, 3H), 4.21 (s, 2H), 4.55 (s, 2H), 7.01 (d, 2H), 7.19 (s, 1H), 7.40 (m, 4H).

LRMS: m/z ES+401 [M+Na]$^+$.

Microanalysis found: C, 61.55; H, 4.07; N, 14.21.

C$_{20}$H$_{15}$ClN$_4$O$_2$;0.5H$_2$O requires C, 61.94; H, 4.16; N, 14.45%.

Example 2

3-Chloro-5-[3-methyl-5-(7-oxo-5,7-dihydro-pyrrolo[3,4-b]pyridin-6-ylmethyl)-1H-pyrazol-4-yloxy]-benzonitrile

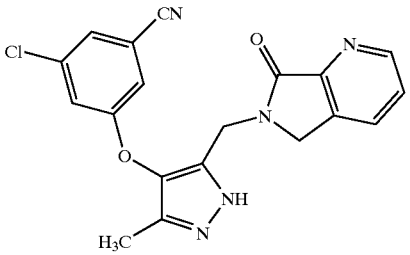

Sodium triacetoxyborohydride (65 mg, 0.3 mmol) followed by acetic acid (17 μg, 0.3 mmol) were added to the amine of preparation 13 (75 mg, 0.29 mmol) and the aldehyde from preparation 16 (60 mg, 3.1 mmol) in dichloromethane (5 ml), and the reaction stirred at room temperature for 18 hours. The mixture was evaporated under reduced pressure and the residue purified by chromatography on silica gel using an elution gradient of dichloromethane:methanol:0.88 ammonia (100:0:0 to 90:10:1) to afford the title compound as a white solid (50 mg).

$^1$H NMR (400 MHz, DMSO-d$_6$): δ 2.03 (s, 3H), 4.27 (s, 2H), 4.60 (s, 2H), 7.03 (s, 1H), 7.10 (s, 1H), 7.29 (s, 1H), 7.48 (m, 1H), 7.90 (m, 1H), 8.59 (m, 1H), 12.7 (br s, 1H).

LRMS: m/z APCI 380 [M+H]$^+$.

Example 3

3-Chloro-5-[3-methyl-5-(5-oxo-5,7-dihydro-pyrrolo[3,4-b]pyridin-6-ylmethyl)-1H-pyrazol-4-yloxy]-benzonitrile

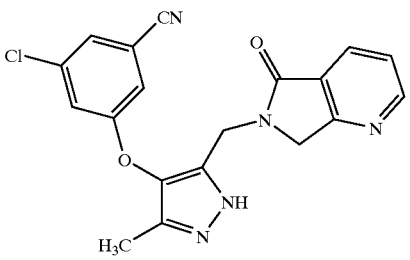

Sodium carbonate (100 mg, 0.91 mmol) followed by the bromide of preparation 15 (107 mg, 0.38 mmol) were added to a solution of the amine of preparation 13 (100 mg, 0.38 mmol) in N,N-dimethylformamide (5 ml), and the reaction stirred at room temperature for 3 hours. TLC analysis showed starting material remaining, so additional bromide (940 mg, 0.14 mmol) was added, and the reaction stirred for a further 4 days. The mixture was concentrated under reduced pressure, the residue azeotroped with toluene, then dissolved in ethyl acetate (50 ml). This solution was washed with water (2×30 ml) and brine (20 ml), then dried over magnesium sulphate and evaporated under reduced pressure.

The crude product was purified by chromatography on silica gel using an elution gradient of dichloromethane:methanol:0.88 ammonia (100:0:0 to 90:10:1). The product was then recrystallised from acetonitrile to afford the title compound (20 mg). mp-225–227° C.

$^1$H NMR (400 MHz, DMSO-d$_6$): δ 2.03 (s, 3H), 4.29 (s, 2H), 4.61 (s, 2H), 7.05 (s, 1H), 7.11 (s, 1H), 7.27 (s, 1H), 7.40 (m, 1H), 7.82 (d, 1H), 8.65 (d, 1H), 12.69 (br s, 1H).

Microanalysis found: C, 59.00; H, 3.61; N, 18.19. $C_{19}H_{14}ClN_5O_2;0.5H_2O$ requires C, 58.69; H, 3.89; N, 18.01%.

Example 4

5-[3-Methyl-5-(1-oxo-1,3-dihydro-isoindol-2-ylmethyl)-1H-pyrazol-4-yloxy]-isophthalonitrile

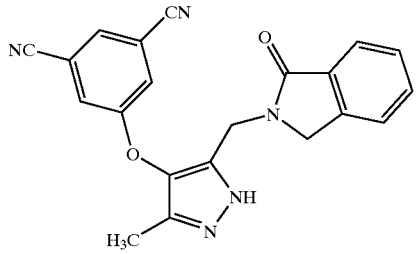

Sodium triacetoxyborohydride (110 mg, 0.52 mmol) was added to a solution of acetic acid (30 μl, 0.47 mmol), the amine from preparation 14 (120 mg, 0.47 mmol) and methyl 2-formylbenzoate (Maybridge) (81 mg, 0.5 mmol) in dichloromethane (5 ml) and tetrahydrofuran (3 ml) and the reaction stirred at room temperature for 2 hours. The reaction was diluted with dichloromethane (40 ml), and washed with sodium carbonate (10 ml) solution. This aqueous solution was extracted with further dichloromethane (20 ml), and the combined organic solutions then washed with brine, dried over magnesium sulphate and evaporated under reduced pressure. The residue was purified by chromatography on silica gel using an elution gradient of dichloromethane:methanol:0.88 ammonia (100:0:0 to 95:5:0.5) and the product recrystallised from ethyl acetate and acetonitrile to afford the title compound.

$^1$H NMR (400 MHz, DMSO-$d_6$): δ 2.02 (s, 3H), 4.23 (s, 2H), 4.56 (s, 2H), 7.36–7.63 (m, 7H), 12.75 (br s, 1H).

LRMS: m/z ES+ 392 [M+Na]$^+$.

Mp-247–248° C. Microanalysis found: C, 67.69; H, 4.05; N, 18.77. $C_{21}H_{15}N_5O_2;0.5H_2O$ requires C, 67.63; H, 4.16; N, 18.78%.

Example 5

5-[5-(6-Cyano-1-oxo-1,3-dihydro-isoindol-2-ylmethyl)-3-methyl-1H-pyrazol-4-yloxy]-isophthalonitrile

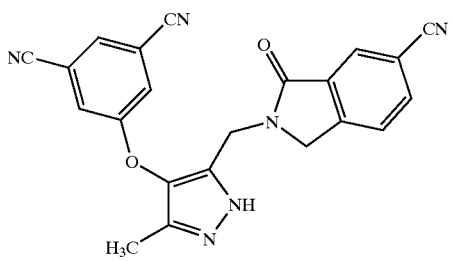

Sodium carbonate (301 mg, 2.84 mmol) was added to a suspension of the amine of preparation 14 (300 mg, 1.18 mmol) in N,N-dimethylformamide (10 ml), and the mixture stirred at 40° C. for 30 minutes. 2-Bromomethyl-5-cyano-benzoic acid methyl ester (WO 0234745, line 12, pg 49) (300 mg, 1.18 mmol) was added, and the reaction stirred at 30° C. for 18 hours. The mixture was concentrated under reduced pressure and the residue partitioned between ethyl acetate (25 ml) and water (25 ml). The resulting precipitate was filtered off and dried to afford the title compound as a white solid (160 mg).

$^1$H NMR (400 MHz, DMSO-$d_6$): δ 2.00 (s, 3H), 4.40 (s, 2H), 4.60 (s, 2H), 7.50 (s, 2H), 7.60 (d, 1H), 7.70 (s, 1H), 7.80 (s, 1H), 8.00 (d, 1H).

Microanalysis found: C, 65.38; H, 3.62; N, 20.64. $C_{22}H_{14}N_6O_2;0.5H_2O$ requires C, 65.50; H, 3.75; N, 20.83%.

Example 6

5-[5-(5-Cyano-1-oxo-1,3-dihydro-isoindol-2-ylmethyl)-3-methyl-1H-pyrazol-4-yloxy]-isophthalonitrile

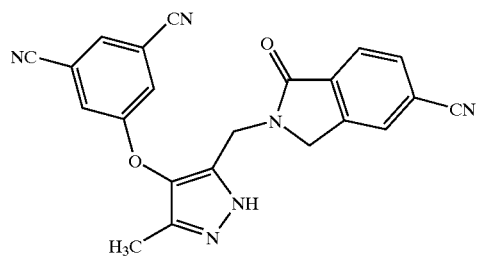

Sodium carbonate (401 mg, 3.78 mmol) was added to the amine from preparation 14 (400 mg, 1.6 mmol) in N,N-dimethylformamide (20 ml), followed by 2-bromomethyl-4-cyano-benzoic acid methyl ester (EP 685478, reference example 21) (340 mg, 1.6 mmol) and the reaction stirred at room temperature for 18 hours. The reaction was then warmed to 40° C. for a further 3 hours, the mixture was concentrated under reduced pressure and the residue partitioned between ethyl acetate (25 ml) and water (25 ml). The layers were separated, the organic phase dried over magnesium sulphate and evaporated under reduced pressure. The crude product was purified by chromatography using a Bond Elut Si cartridge and dichloromethane:methanol:0.88 ammonia (100:0:0 to 90:10:1) as the eluant. The product was then triturated with hot acetonitrile, the solid filtered and dried to afford the title compound as a white solid (48.5 mg).

$^1$H NMR (400 MHz, DMSO-$d_6$): 2.02 (s, 3H), 4.36 (s, 2H), 4.60 (s, 2H), 7.42 (s, 2H), 7.50 (d, 1H), 7.70 (s, 1H), 7.82 (m, 1H), 7.97 (s, 1H), 12.75 (brs, 1H).

LRMS: m/z ES– 393 [M–H]$^-$.

Microanalysis found: C, 65.55; H, 3.57; N, 21.03. $C_{22}H_{14}N_6O_2;0.5H_2O$ requires C, 65.50; H, 3.75; N, 20.83%.

Preparation 1

1-Bromo-3-chloro-5-methoxybenzene

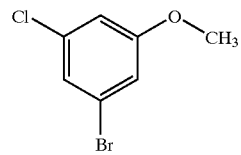

Sodium methoxide (4.5M solution in methanol, 2.20 ml, 10.0 mmol) was added dropwise to a stirred solution of 1-fluoro-3-chloro-5-bromobenzene (1.00 g, 4.77 mmol) in methanol (28 ml) at room temperature under a nitrogen atmosphere. The mixture was heated under reflux for 3 days and then cooled to room temperature. The mixture was evaporated under reduced pressure and the resulting yellow oil was dissolved in dichloromethane (30 ml). The dichloromethane solution was washed with water (2×20 ml) dried over magnesium sulphate, filtered and evaporated under reduced pressure. The residue was purified by chromatography on silica gel eluting with cyclohexane to provide the title compound as a colourless oil (302 mg).

$^1$H-NMR (400 MHz, CDCl$_3$): δ 3.77 (s, 3H), 6.82 (s, 1H), 6.94 (s, 1H), 7.09 (s, 1H).

Microanalysis: Found: C, 37.94; H, 2.75. C$_7$H$_6$BrClO requires; C, 37.96; H, 2.73%.

Preparation 2

1,3-Dibromo-5-methoxybenzene

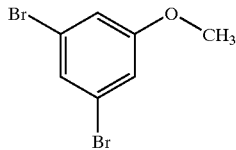

Sodium methoxide (4.5M solution in methanol, 8.80 ml, 41.0 mmol) was added dropwise to a stirred solution of 3,5-dibromofluorobenzene (5.00 g, 19.0 mmol) in N,N-dimethylformamide (95 ml) at 0° C. under a nitrogen atmosphere. The reaction was warmed to room temperature, stirred for 1 hour and then evaporated under reduced pressure. The residue was dissolved in diethyl ether and was washed with water (3×300 ml) and brine (300 ml), dried over magnesium sulphate, filtered and concentrated under reduced pressure to give the title compound as a white solid (5.13 g).

$^1$H-NMR (300 MHz, CDCl$_3$): δ 3.79 (s, 3H), 7.00 (s, 2H), 7.26 (s, 1H).

LRMS: m/z TS+ 266 [M+H]$^+$.

Preparation 3

3-Chloro-5-methoxybenzonitrile

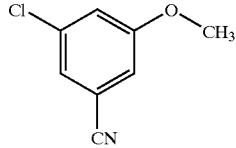

Tetrakis(triphenylphosphine)palladium (0) (174 mg, 0.15 mmol) was added in one portion to a stirred solution of the bromide of Preparation 1 (500 mg, 2.26 mmol) and zinc cyanide (146 mg, 1.24 mmol) in N,N-dimethylformamide (3 ml) at room temperature under a nitrogen atmosphere. The reaction was heated at 100° C. for 14 hours and then cooled to room temperature. The solvent was evaporated under reduced pressure and the residue was purified by chromatography on silica gel using ethyl acetate in cyclohexane as eluant (5:95) to provide the title compound as a yellow oil (380 mg).

$^1$H-NMR (300 MHz, CDCl$_3$): δ 3.82 (s, 3H), 7.04 (s, 1H), 7.12 (s, 1H), 7.23 (s, 1H).

Preparation 4

3,5-Dicyanomethoxybenzene

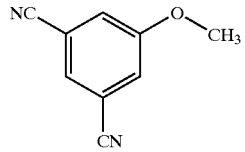

Tris(dibenzylideneacetone)dipalladium(0) (6.53 g, 7.15 mmol) was added in one portion to a stirred solution of the bromide of Preparation 2 (38.0 g, 143 mmol), 1,1'-bis(diphenylphosphino)ferrocene (9.3 g, 16.8 mmol) and zinc cyanide (20.0 g, 172 mmol) in N,N-dimethylformamide (300 ml) at room temperature under nitrogen. The reaction was heated at 100° C. for 14 hours and cooled to room temperature. Water (1500 ml) was added and the mixture was extracted with ethyl acetate (3×500 ml). The combined organics were filtered and the filtrate was washed with water (500 ml), dried over magnesium sulphate, filtered and concentrated under reduced pressure. The resulting solid was triturated with toluene (1000 ml) to provide the title compound (18.0 g) as a tan solid.

$^1$H-NMR (300 MHz, CDCl$_3$): δ 3.83 (s, 3H), 7.31 (s, 2H), 7.48 (s, 1H).

Preparation 5

3-Chloro-5-hydroxybenzonitrile

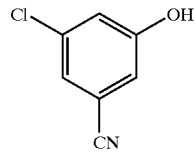

Boron trichloride (1.0M solution in dichloromethane, 26.0 ml, 26.0 mmol) was added dropwise to a stirred solution of the nitrile of Preparation 3 (1.80 g, 10.0 mmol) and tetrabutylammonium iodide (4.36 g, 11.0 mmol) in dichloromethane (50 ml) at −78° C. The reaction mixture was warmed to room temperature and stirred for 14 hours. The reaction mixture was cooled to 0° C. and ice and dichloromethane (100 ml) were added. The organic phase was washed with water (3×40 ml) and brine (40 ml), dried over magnesium sulphate, filtered and concentrated under reduced pressure. The residue was purified by chromatography on silica gel using ethyl acetate in cyclohexane as eluant (20:80) to give the title compound as a white solid (900 mg).

$^1$H-NMR (400 MHz, DMSO-d$_6$): δ 7.12 (m, 2H), 7.38 (s, 1H), 10.65 (s, 1H).

Microanalysis: Found: C, 54.76; H, 2.81; N, 8.94. C$_7$H$_4$ClNO requires; C, 54.75; H, 2.63; N, 9.12%.

Preparation 6

3,5-Dicyanohydroxybenzene

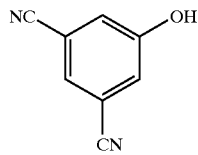

The ether of Preparation 4 (9.60 g, 60.7 mmol) was added portionwise to a stirred suspension of aluminium trichloride (32.4 g, 243 mmol) in dichloromethane (250 ml) at 0° C. under a nitrogen atmosphere. The suspension was stirred at 45° C. for 6 days, then cooled to room temperature and poured onto ice (450 ml). Concentrated hydrochloric acid (450 ml) was added dropwise and the resulting suspension was stirred for 10 minutes at room temperature. The solid formed was isolated by filtration, washed with water and dried over phosphorus pentoxide to give the title compound as a tan solid (7.83 g).

$^1$H-NMR (400 MHz, CDCl$_3$): δ 7.36 (m, 2H), 7.56 (m, 1H).

Preparation 7

3-[(3,5-Dimethyl-1H-pyrazol-4-yl)oxy]-5-chlorobenzonitrile

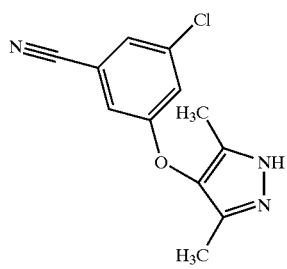

A mixture of 3-chloro-2,4-pentanedione (6.73 g, 50.0 mmol), the phenol of Preparation 5 (7.67 g, 50.0 mmol), caesium carbonate (18.0 g, 55.4 mmol) and acetone (40 ml) was heated under reflux for 2 hours. The reaction was cooled to room temperature, N,N-dimethylformamide (6 ml) and acetone (30 ml) were added and the reaction was heated at 70° C. for a further 12 hours. The mixture was cooled to room temperature and the solid was removed by filtration and dissolved in 1M aqueous hydrochloric acid (150 ml). The aqueous solution was extracted with dichloromethane (3×100 ml) and the combined organic phases were washed with brine (30 ml), dried over magnesium sulphate, filtered and concentrated under reduced pressure to give a brown solid (5.5 g).

This was suspended in acetic acid (22 ml), hydrazine hydrate (1.1 ml, 22 mmol) added, and the reaction stirred at room temperature for 18 hours. The mixture was concentrated under reduced pressure and the residue purified by chromatography on silica gel using an elution gradient of dichloromethane:ethyl acetate (100:0 to 85:15) to afford the title compound, (4.8 g).

$^1$H-NMR (400 MHz, CDCl$_3$): δ 2.09 (s, 6H), 7.02 (m, 1H), 7.10 (m, 1H), 7.25 (m, 1H).

Microanalysis found: C, 57.86; H, 4.03; N, 16.78. C$_{12}$H$_{10}$ClN$_3$O requires C, 58.19; H, 4.07; N, 16.97%.

Preparation 8

5-(3,5-Dimethyl-1H-pyrazol-4-yloxy)-isophthalonitrile

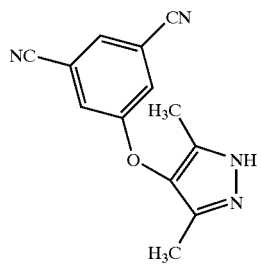

The phenol from preparation 6 (2 g, 13.8 mmol) was mixed with 3-chloro-2,4-pentanedione (2 ml, 16.7 mmol) and caesium carbonate (4.51 g, 13.8 mmol) in acetone (50 ml), and was heated at 65° C. for 2 hours. The mixture was cooled to room temperature and concentrated hydrochloric acid (2 ml) was added. The mixture was diluted with water (50 ml) and extracted with ethyl acetate (3×50 ml). The combined organic solutions were washed with brine, dried over magnesium sulphate and evaporated under reduced pressure. The residual yellow oil was dissolved in acetic acid (30 ml) and hydrazine (1 ml, 20.7 mmol) was added. The mixture was stirred at room temperature for 10 minutes and then evaporated under reduced pressure. The residue was dissolved in ethyl acetate (50 ml) and washed with 10% sodium carbonate solution (30 ml), water (30 ml), brine (30 ml) and then dried over magnesium sulphate. The solvent was evaporated under reduced pressure and the residue was triturated with diethyl ether to give the title compound as a pale yellow solid (1.8 g).

m.p.182–185° C.; LRMS: m/z TS+ 239 [M+H]$^+$ $^1$H-NMR (300 MHz, CDCl$_3$): δ 2.16 (s, 6H), 7.40 (s, 2H), 7.59 (s, 1H).

Preparation 9

3-[(1-Acetyl-3,5-dimethyl-1H-pyrazol-4-yl)oxy]-5-chlorobenzonitrile

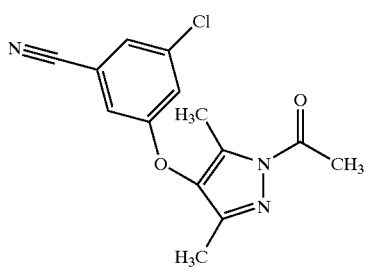

Sodium hydride (60% dispersion in oil, 840 mg, 21.0 mmol) was added to a stirred solution of acetyl chloride (1.50 ml, 21.0 mmol) and the pyrazole of Preparation 7 (4.80 g, 19.4 mmol) in N,N-dimethylformamide (20 ml) at 0° C. under a nitrogen atmosphere. The reaction was stirred at 0° C. for 15 minutes and then water (200 ml) was added. The aqueous mixture was extracted with ethyl acetate (3×120 ml). The combined organic phases were washed with water (50 ml) and brine (50 ml), dried over magnesium sulphate, filtered and evaporated under reduced pressure to leave a yellow solid. The crude product was purified by chromatography on silica gel using dichloromethane as eluant to give the title compound as a white solid (5.00 g).

¹H-NMR (400 MHz, CDCl₃): δ 2.06 (s, 3H), 2.38 (s, 3H), 2.65 (s, 3H), 6.99 (m, 1H), 7.08 (m, 1H), 7.29 (m, 1H).

LRMS: m/z TS+ 290 [M+H]⁺.

Preparation 10

5-[1-Acetyl-3,5-dimethyl-1H-pyrazol-4-yloxy]-isophthalonitrile

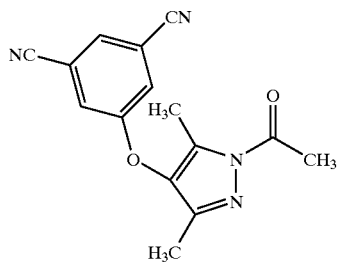

The pyrazole from preparation 8 (1.75 g, 7.35 mmol) was dissolved in N,N-dimethylformamide (15 ml) and was cooled to 0° C. Acetyl chloride (0.78 ml, 11.03 mmol) and then sodium hydride (60% in mineral oil, 441 mg, 11.03 mmol) were added. The mixture was stirred at 0° C. for 15 minutes and then a saturated solution of ammonium chloride (10 ml) was added. The reaction mixture was extracted with ethyl acetate (3×50 ml) and the combined organic layers were washed with water (50 ml) and brine (200 ml) dried over magnesium sulphate and evaporated under reduced pressure. The residue was triturated with ether to afford the title compound as a white solid, (1.5 g).

¹H-NMR (400 MHz, CDCl₃): δ 2.06 (s, 3H), 2.38 (s, 3H), 2.66 (s, 3H), 7.33 (s, 2H), 7.56 (s, 1H).

LRMS: m/z TS+ 281.2 [M+H]⁺.

Preparation 11

3-{[1-Acetyl-3-(bromomethyl)-5-methyl-1H-pyrazol-4-yl]oxy}-5-chlorobenzonitrile

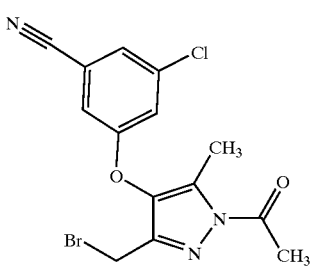

N-Bromosuccinimide (4.60 g, 25.6 mmol) was added to a stirred solution of the pyrazole of Preparation 9 (5.00 g, 17.3 mmol) and azobisisobutyronitrile (20 mg) in 1,1,1-trichloroethane (70 ml) at room temperature under a nitrogen atmosphere. The reaction was heated at 80° C. for 3 hours and then cooled to room temperature. A second portion of N-bromosuccinimide (2.0 g, 11.2 mmol) was added and the reaction mixture was heated at 80° C. for 4 hours. The reaction was cooled to room temperature, evaporated under reduced pressure and the resulting yellow oil was purified by chromatography on silica gel using pentane in dichloromethane as eluant (25:75) to give the title compound as a white solid (2.30 g).

m.p. 122–123° C.

¹H-NMR (400 MHz, CDCl₃): δ 2.10 (s, 3H), 2.74 (s, 3H), 4.73 (s, 2H), 7.12 (s, 1H), 7.22 (s, 1H), 7.39 (s, 1H).

Preparation 12

5-[1-Acetyl-5-bromomethyl-3-methyl-1H-pyrazol-4-yloxy]-isophthalonitrile

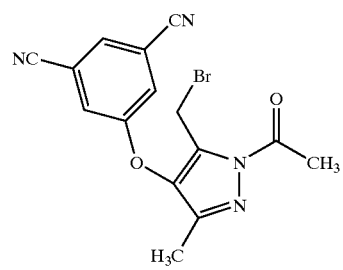

A solution of the pyrazole of preparation 10 (1.45 g, 5.18 mmol) and N-bromo succinimide (1.38 g, 7.76 mmol) in carbon tetrachloride (50 ml) was purged with nitrogen for 20 minutes. 2,2-Azobis(isobutyronitrile) (catalytic) was added and the mixture was heated at 95° C. for 1 hour. The solvent was evaporated under reduced pressure and the residue was purified by chromatography on silica gel using ethyl acetate in pentane (80:20) as eluant to give the title compound as a white solid (1.7 g).

¹H-NMR (400 MHz, CDCl₃): δ 2.06 (s, 3H), 2.66 (s, 3H), 4.67 (s, 2H), 7.40 (s, 2H), 7.63 (s, 1H).

Preparation 13

3-(5-Aminomethyl-3-methyl-1H-pyrazol-4-yloxy)-5-chlorobenzonitrile

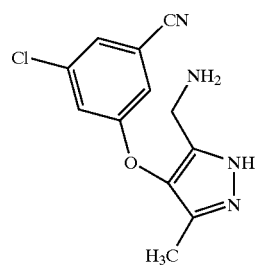

The bromide of Preparation 11 (300 mg, 0.80 mmol) was added to a saturated solution of ammonia in isopropanol (50 ml) at 0° C. The reaction was stirred for 2 hours and allowed to slowly warm to room temperature. The mixture was concentrated under reduced pressure and the resulting yellow oil was dissolved in dichloromethane (50 ml). The dichloromethane was washed with 1M aqueous sodium carbonate solution (20 ml), dried over magnesium sulphate, filtered and concentrated under reduced pressure to provide the title compound (220 mg) as a white foam.

¹H-NMR (300 MHz, CDCl₃): δ 2.14 (s, 3H), 3.79 (s, 2H), 7.08 (s, 1H), 7.16 (s, 1H), 7.31 (s, 1H).

LRMS (thermospray): m/z 263 [M+H⁺].

Preparation 14

5-(5-Aminomethyl-3-methyl-1H-pyrazol-4-yloxy)-isophthalonitrile

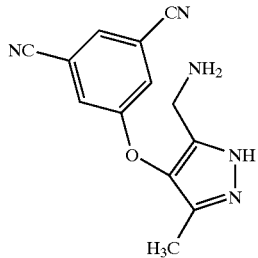

The bromide of preparation 12 (1 g, 2.8 mmol) was added to a freshly prepared solution of iso-propanol (100 ml) saturated with ammonia, and the reaction stirred at room temperature for 3 hours. The mixture was concentrated under reduced pressure and the residue partitioned between 10% aqueous potassium carbonate solution and dichloromethane. The aqueous phase was extracted further with dichloromethane and then ethyl acetate. The combined organic solutions were dried over magnesium sulphate and concentrated under reduced pressure. The crude product was purified by chromatography on silica gel using dichloromethane:methanol:0.88 ammonia (93:7:1) as eluant to afford the title compound as a white solid (316 mg).

$^1$H-NMR (400 MHz, DMSO-$d_6$): δ 1.98 (s, 3H), 3.50 (s, 2H), 7.72 (s, 2H), 8.08 (s, 1H).

LRMS: m/z ES+ 254 [M+H]$^+$.

Preparation 15

2-Bromomethyl-pyridine-3-carboxylic acid ethyl ester hydrochloride

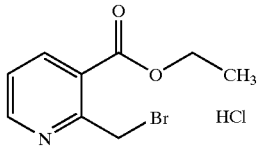

A mixture of ethyl 2-methylnicotinate (5.0 g, 30.3 mmol), N-bromosuccinimide (7.5 g, 42.1 mmol) and benzoyl peroxide (0.5 g) in carbon tetrachloride (100 ml) was heated under reflux for 6 hours, then allowed to cool. The resulting mixture was filtered, the filtered solid washed with carbon tetrachloride, and the combined filtrate washed with 4% sodium hydroxide solution, water and 2% hydrochloric acid, then dried over sodium sulphate. The solution was then treated with ethereal hydrochloric acid, and the resulting precipitate was filtered off, washed with ether and dried to afford the title compound as a pale yellow solid (4.5 g).

$^1$H NMR (60 MHz, DMSO-$d_6$): δ 1.40 (t, 3H), 4.42 (q, 2H), 5.02–5.22 (m, 2H), 7.70 (m, 1H), 8.40 (m, 1H), 8.80 (m, 1H), 10.20 (s, 1H).

Preparation 16

3-Formyl-pyridine-2-carboxylic acid ethyl ester

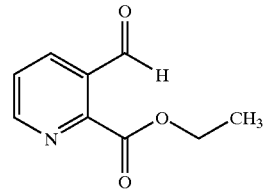

Triethylamine (1.4 ml, 10 mmol) was added to a solution of 2-bromopyridine-3-carbaldehyde (Synthesis 1999; (2); 306) (1.5 g, 8.0 mmol), tetrakis(triphenylphosphine)palladium (0) (470 mg, 0.4 mmol) in ethanol (50 ml), and this mixture heated to 100° C. under an atmosphere of carbon monoxide in a sealed vessel for 16 hours. The cooled reaction mixture was concentrated under reduced pressure and the residue partitioned between ethyl acetate (50 ml) and 2N hydrochloric acid (20 ml). The layers were separated, the aqueous phase extracted with further ethyl acetate (50 ml), and the combined organic solutions dried over magnesium sulphate and evaporated under reduced pressure. The crude product was purified by chromatography on silica gel using an elution gradient of pentane:ethyl acetate (66:34 to 50:50) to afford the title compound, (130 mg).

$^1$H NMR (400 MHz, CDCl$_3$): δ 1.48 (t, 3H), 4.53 (q, 2H), 7.61 (m, 1H), 8.25 (d, 1H), 8.87 (d, 1H), 10.60 (s, 1H).

What is claimed is:
1. A compound at formula (I)

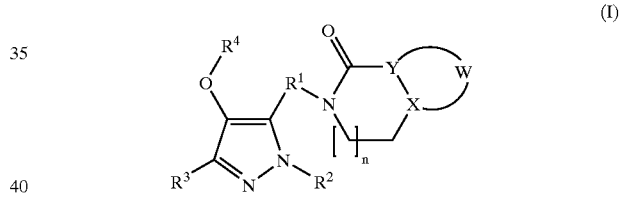

(I)

or a pharmaceutically acceptable salt, solvate or derivative thereof, wherein:

W—X—Y defines a five or six-membered partially saturated or aromatic ring containing 0 to 3 nitrogen atoms wherein X is CH or N and Y is CH or, when X is CH, may also be N; said ring being optionally substituted by halo, oxo, —CN, —COR$^5$, —CONR$^5$R$^5$, —SO$_2$NR$^5$R$^5$, —NR$^5$SO$_2$R$^5$, —OR$^5$, OR$^{11}$, —NR$^5$R$^5$, —(C$_1$–C$_6$ alkylene)-NR$^5$R$^5$, R$^7$, R$^{11}$, or CF$_3$;

R$^1$ is C$_1$–C$_6$ alkylene;

R$^2$ is H, C$_1$–C$_6$ alkyl, C$_3$–C$_6$ alkenyl, C$_3$–C$_6$ alkynyl, C$_3$–C$_7$ cycloalkyl, C$_3$–C$_7$ cycloalkenyl, phenyl, benzyl, R$^8$ or R$^9$, said C$_1$–C$_6$ alkyl, C$_3$–C$_7$ cycloalkyl, phenyl and benzyl being optionally substituted by halo, —OR$^5$, —OR$^{10}$, —CN, —CO$_2$R$^7$, —OCONR$^5$R$^5$, —CONR$^5$R$^5$, —C(=NR$^5$)NR$^5$OR$^5$, —CONR$^5$NR$^5$R$^5$, —NR$^6$R$^6$, —NR$^5$R$^{10}$, —NR$^5$COR$^5$, —NR$^5$COR$^8$, —NR$^5$COR$^{10}$, —NR$^5$CO$_2$R$^5$, —NR$^5$CONR$^5$R$^5$, —SO$_2$NR$^5$R$^5$, —NR$^5$SO$_2$R$^5$, —NR$^5$SO$_2$NR$^5$R$^5$, R$^8$ or R$^9$;

R$^3$ is H, C$_1$–C$_6$ alkyl, C$_3$–C$_7$ cycloalkyl, phenyl, benzyl, halo, —CN, —OR$^7$, —CO$_2$R$^5$, —CONR$^5$R$^5$, R$^8$ or R$^9$, said C$_1$–C$_6$ alkyl, C$_3$–C$_7$ cycloalkyl, phenyl and benzyl being optionally substituted by halo, —CN, —OR$^5$, —CO$_2$R$^5$, —CONR$^5$R$^5$, —OCONR$^5$R$^5$, —NR$^5$CO$_2$R$^5$, —NR$^6$R$^6$, —NR$^5$COR$^5$, —SO$_2$NR$^5$R$^5$, —NR$^5$CONR$^5$R$^5$, —NR$^5$SO$_2$R$^5$, R$^8$ or R$^9$;

R$^4$ is phenyl, naphthyl or pyridyl, each being optionally substituted by R$^8$, halo, —CN, C$_1$–C$_6$ alkyl, C$_1$–C$_6$ haloalkyl, C$_3$–C$_7$ cycloalkyl, C$_1$–C$_6$ alkoxy, —CONR$^5$R$^5$, OR$^{11}$, So$_x$R$^6$, O—(C$_1$–C$_6$ alkylene)-CONR$^5$R$^5$, O—(C$_1$–C$_6$ alkylene)-NR$^5$R$^5$, or O—(C$_1$–C$_6$ alkylene)-OR$^8$;

each R$^5$ is independently either H, C$_1$–C$_6$ alkyl or C$_3$–C$_7$ cycloalkyl or, when two R$^5$ groups are attached to the same nitrogen atom, those two groups taken together with the nitrogen atom to which they are attached represent azetidinyl, pyrrolidinyl, pipendinyl, homopiperidinyl, piperazinyl, homopiperazinyl or morpholinyl, said azetidinyl, pyrrolidinyl, piperidinyl, homopiperidinyl, piperazinyl, homopiperazinyl and morpholinyl being optionally substituted by C$_1$–C$_6$ alkyl or C$_3$–C$_7$ cycloalkyl;

each R$^6$ is independently either H, C$_1$–C$_6$ alkyl or C$_3$–C$_7$ cycloalkyl;

R$^7$ is C$_1$–C$_6$ alkyl or C$_3$–C$_7$ cycloalkyl;

R$^8$ is a five or six-membered, aromatic heterocyclic group containing (i) from 1 to 4 nitrogen heteroatom(s) or (ii) 1 or 2 nitrogen heteroatom(s) and 1 oxygen or 1 sulphur heteroatom or (iii) 1 or 2 oxygen or sulphur heteroatom(s), said heterocyclic group being optionally substituted by halo, oxo, —CN, —COR$^5$, —CONR$^5$R$^5$, —SO$_2$NR$^5$R$^5$, —NR$^5$SO$_2$R$^5$, —OR$^5$, —NR$^5$R$^5$, —(C$_1$–C$_6$ alkylene)-NR$^5$R$^5$, C$_1$–C$_6$ alkyl, fluoro(C$_1$–C$_6$)alkyl or C$_3$–C$_7$ cycloalkyl;

R$^9$ is a four to seven-membered, saturated or partially unsaturated heterocyclic group containing (i) 1 or 2 nitrogen heteroatom(s) or (ii) 1 nitrogen heteroatom and 1 oxygen or 1 sulphur heteroatom or (iii) 1 oxygen or sulphur heteroatom, said heterocyclic group being optionally substituted by oxo, C$_1$–C$_6$ alkyl, C$_3$–C$_7$ cycloalkyl, —SO$_2$R$^5$, —CONR$^5$R$^5$, —COOR$^5$, —CO—(C$_1$–C$_6$ alkylene)-OR$^5$ or —COR$^5$ and optionally substituted on a carbon atom which is not adjacent to a heteroatom by halo, —OR$^5$, —NR$^5$R$^5$, —NR$^5$COR$^5$, —NR$^5$COOR$^5$, —NR$^5$CONR$^5$R$^5$, —NR$^5$SO$_2$R$^5$ or —CN;

R$^{10}$ is C$_1$–C$_6$ alkyl substituted by R$^8$, R$^9$, —OR$^5$, —CONR$^5$R$^5$, —NR$^5$COR$^5$ or —NR$^5$R$^5$;

R$^{11}$ is phenyl optionally substituted by halo, —CN, —COR$^5$, —CONR$^5$R$^5$, —SO$_2$NR$^5$R$^5$, —NR$^5$SO$_2$R$^5$, —OR$^5$, —NR$^5$R$^5$, —(C$_1$–C$_6$ alkylene)-NR$^5$R$^5$, C$_1$–C$_6$ alkyl, halo(C$_1$–C$_6$)alkyl or C$_3$–C$_7$ cycloalkyl; and x and n are independently 0, 1 or 2.

2. A pharmaceutical composition comprising a compound according to claim 1 and one or more pharmaceutically acceptable excipients, diluents or carriers.

3. A pharmaceutical composition according to claim 2 comprising one or more additional therapeutic agents.

4. A method for inhibiting or modulating HIV reverse transcriptase in a subject in need thereof comprising administering to said subject an effective amount of a compound according to claim 1.

5. A method for inhibiting or modulating HIV reverse transcriptase in a subject in need thereof comprising administering to said subject an effective amount of a pharmaceutical composition according to claim 3.

6. A method for treating an HIV or genetically-related retroviral infection, or a resulting acquired immune deficiency syndrome (AIDS) comprising administering to a subject in need thereof an effective amount of a compound according to claim 1.

7. A method for treating an HIV or genetically-related retroviral infection, or a resulting acquired immune deficiency syndrome (AIDS) comprising administering to a subject in need thereof an effective amount of a pharmaceutical composition according to claim 3.

\* \* \* \* \*